United States Patent
Kurihara

(10) Patent No.: US 11,324,644 B2
(45) Date of Patent: May 10, 2022

(54) ABSORBENT ARTICLE

(71) Applicant: DAIO PAPER CORPORATION, Ehime (JP)

(72) Inventor: Ryoko Kurihara, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 222 days.

(21) Appl. No.: 16/461,108

(22) PCT Filed: Nov. 27, 2017

(86) PCT No.: PCT/JP2017/042347
§ 371 (c)(1),
(2) Date: May 15, 2019

(87) PCT Pub. No.: WO2018/101192
PCT Pub. Date: Jun. 7, 2018

(65) Prior Publication Data
US 2020/0060892 A1 Feb. 27, 2020

(30) Foreign Application Priority Data
Nov. 29, 2016 (JP) .............................. JP2016-231451

(51) Int. Cl.
*A61F 13/511* (2006.01)
*A61F 13/475* (2006.01)

(52) U.S. Cl.
CPC ...... *A61F 13/51104* (2013.01); *A61F 13/475* (2013.01)

(58) Field of Classification Search
CPC ........................ A61F 13/51104; A61F 13/475
See application file for complete search history.

(56) References Cited

U.S. PATENT DOCUMENTS 5,569,234 A * 10/1996 Buell ................ A61F 13/49009
604/396
7,511,186 B2 * 3/2009 Kikuchi .................. A61F 13/42
604/361

(Continued)

FOREIGN PATENT DOCUMENTS

JP  2005-323904  11/2005
JP  2008-289622  12/2008

(Continued)

OTHER PUBLICATIONS

English translation of JP 2009/131442.*
International Search Report dated Jan. 16, 2018 in International (PCT) Application No. PCT/JP2017/042347.

*Primary Examiner* — Adam Marcetich
*Assistant Examiner* — Jessica R Arble
(74) *Attorney, Agent, or Firm* — Wenderoth, Lind & Ponack, L.L.P.

(57) ABSTRACT

An absorbent article, where on a skin side of a laminated part of a side sheet 7 and a liquid permeable front-surface sheet 3, a side emboss that sinks in toward a non-skin side and is made by fusing the side sheet 7 and the liquid permeable front-surface sheet 3 is formed. The side emboss 10 is comprised of a plurality of large embosses 11, where 11 is formed to have a relatively larger area that are arranged to align linearly along the longitudinal direction of a sanitary napkin 1 with equal intervals, and between the adjacent large embosses 11, 11, a plurality of small embosses 12, 12 . . . are formed to have a relatively small area that are arranged in a wave-like shape along the longitudinal direction of the sanitary napkin 1 with intervals, separated from the large embosses 11. A side sheet and a front-surface sheet are strongly joined to prevent detachment, and to improve the feel against the skin by fitting flexibly to a body.

6 Claims, 6 Drawing Sheets

(56) References Cited

U.S. PATENT DOCUMENTS

| | | | | |
|---|---|---|---|---|
| 2008/0249495 | A1* | 10/2008 | Di Virgilio | A61F 13/15731 604/385.01 |
| 2010/0010464 | A1* | 1/2010 | Nishitani | A61F 13/539 604/385.01 |
| 2010/0057031 | A1* | 3/2010 | Kuroda | A61F 13/4756 604/379 |
| 2010/0168707 | A1* | 7/2010 | Nishikawa | A61F 13/4704 604/383 |

FOREIGN PATENT DOCUMENTS

| | | |
|---|---|---|
| JP | 2009-131442 | 6/2009 |
| JP | 2009131442 A * | 6/2009 |
| JP | 2010-125196 | 6/2010 |
| JP | 2013-248309 | 12/2013 |

\* cited by examiner

[Fig. 1]
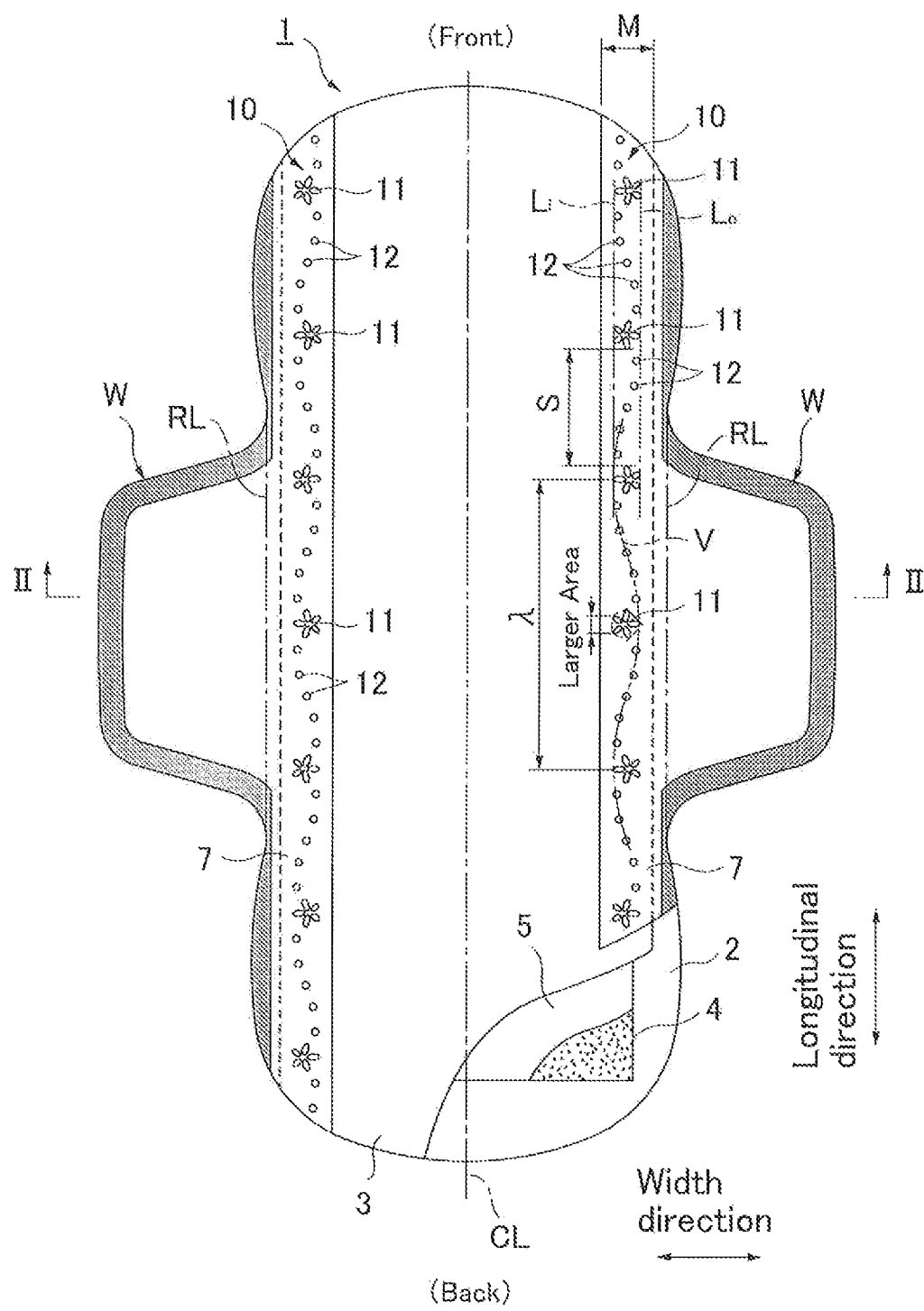

[Fig. 2]
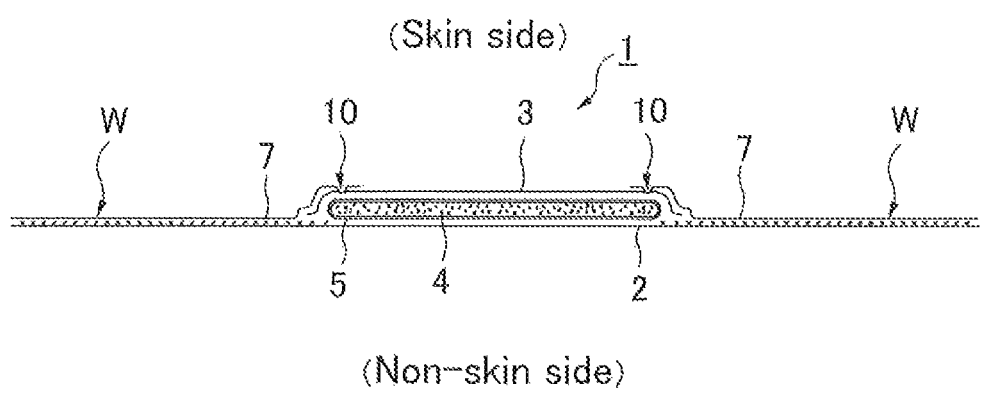

[Fig. 3]
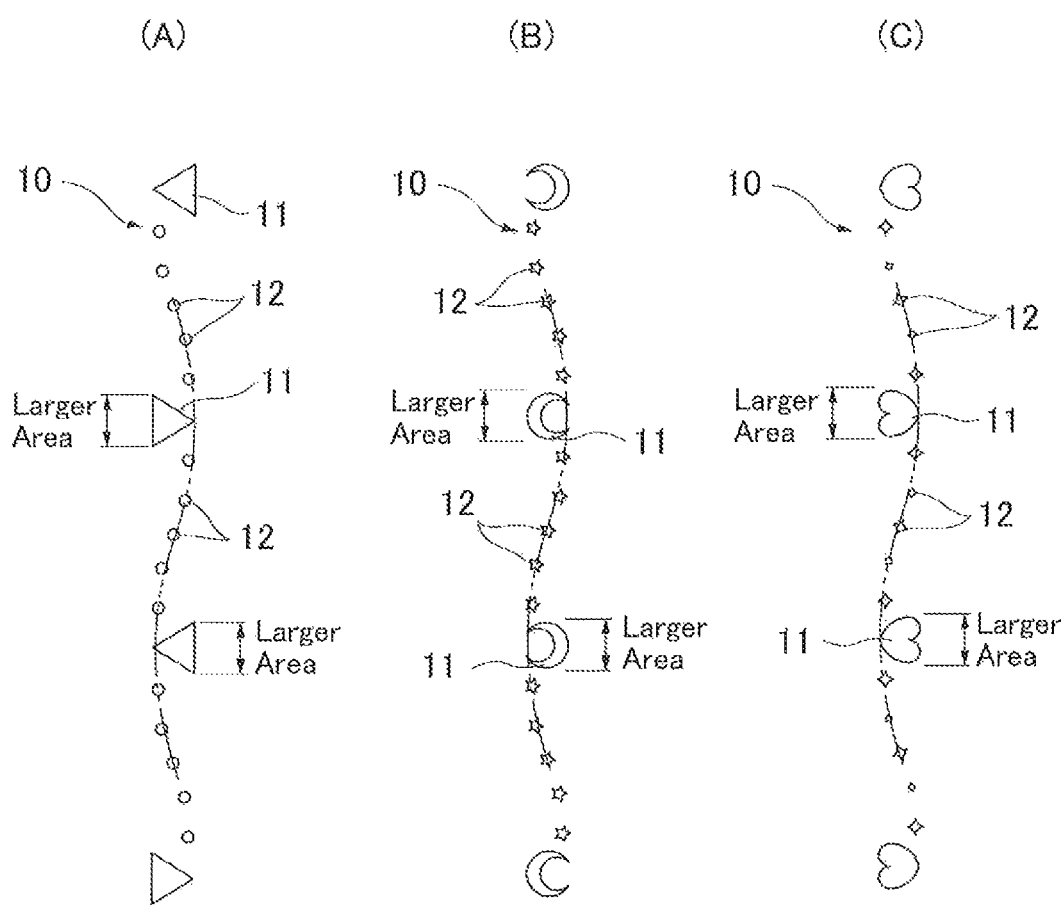

[Fig. 4]
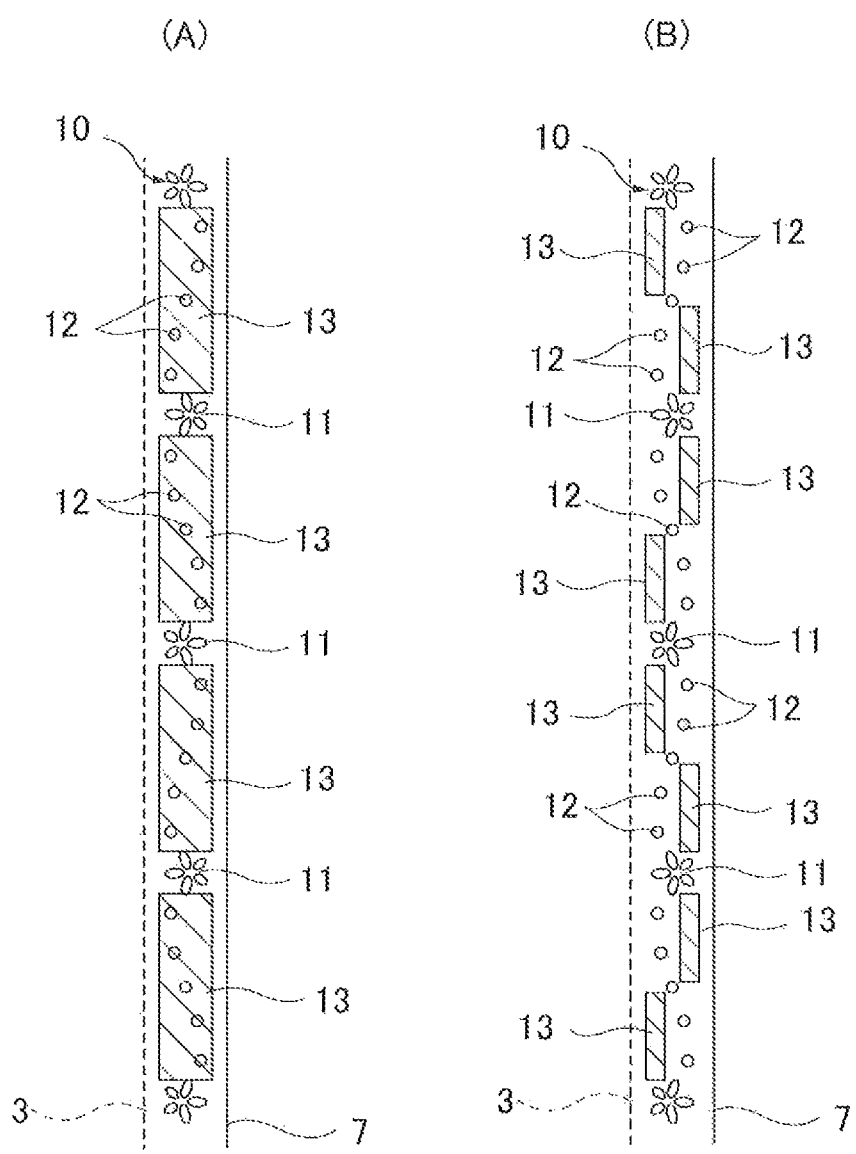

[Fig. 5]
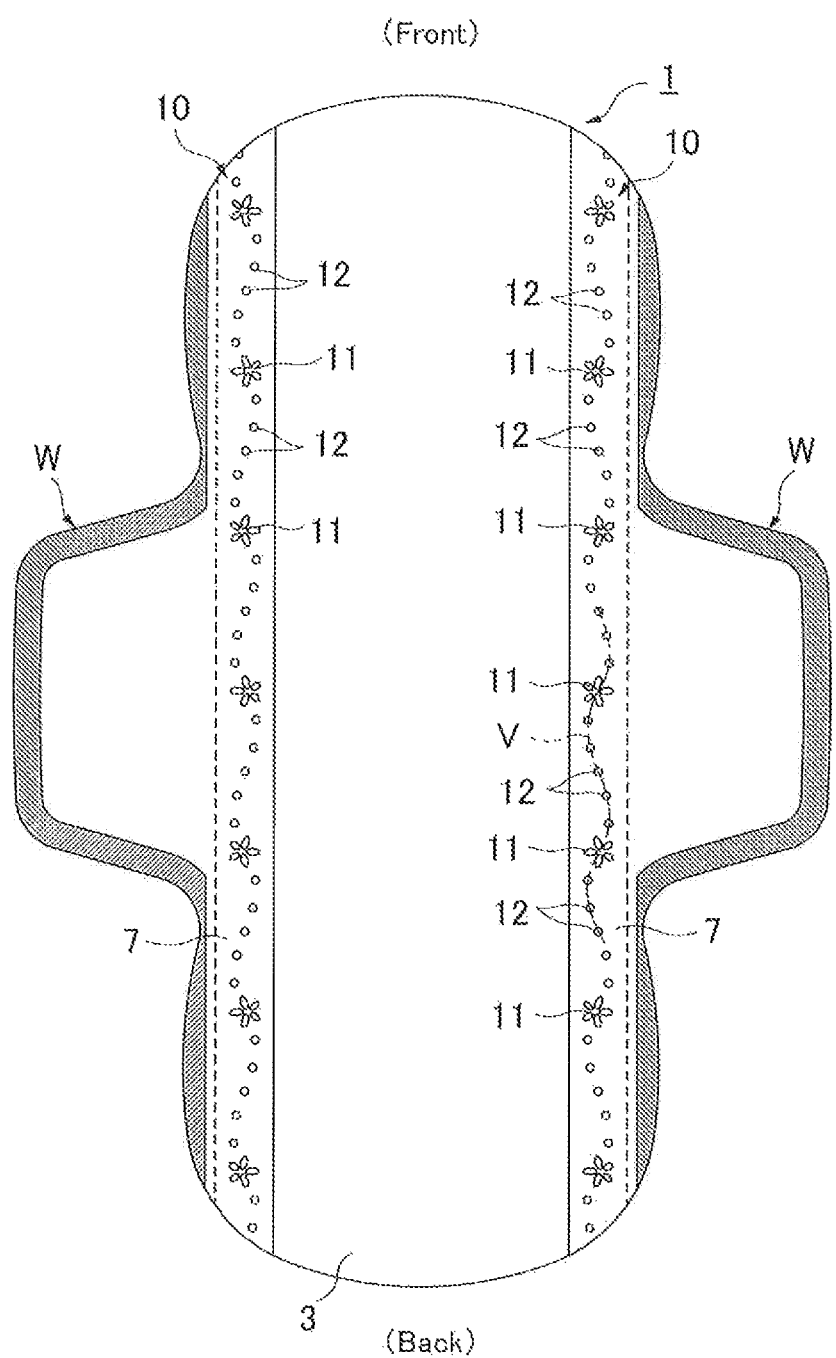

[Fig. 6]
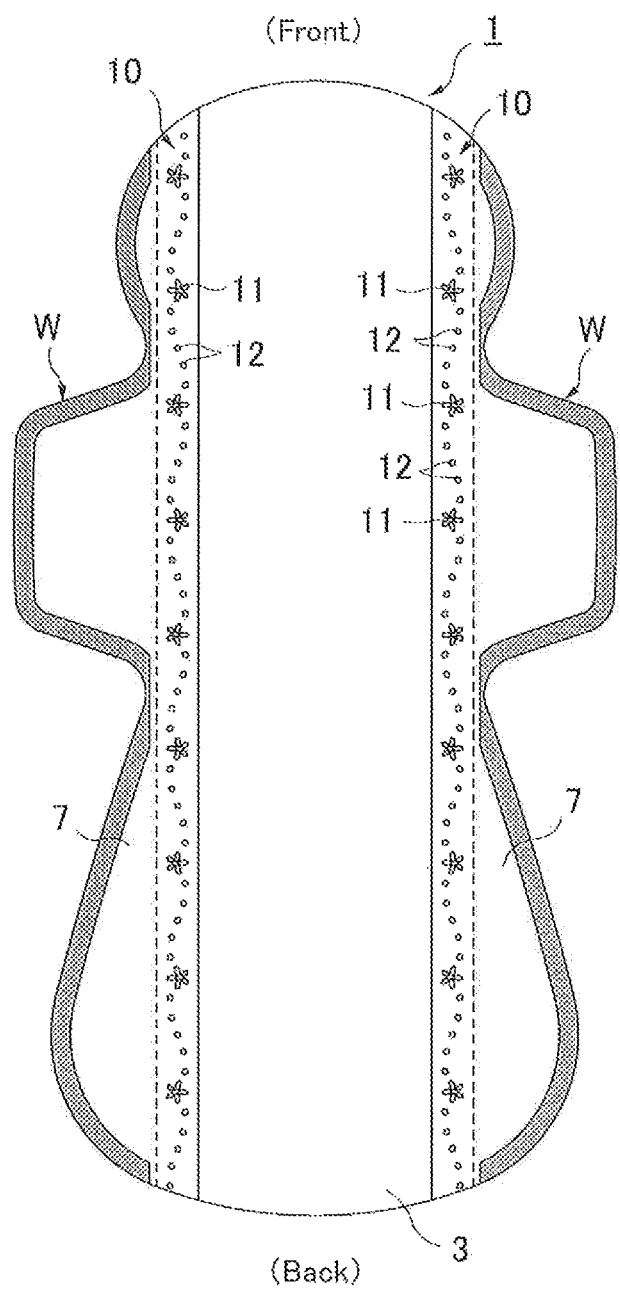

ABSORBENT ARTICLE

TECHNICAL FIELD

The present invention relates to an absorbent article such as a sanitary napkin, a panty liner, and an incontinence pad, and more specifically, to an absorbent article wherein a side sheet is arranged on both side parts of the absorbent article on a skin side along a longitudinal direction, respectively, the side sheet provided with embosses.

BACKGROUND ART

Conventionally, as the absorbent article, an absorbent article wherein an absorber made of cotton-like pulp or the like is interposed between a liquid impermeable back-surface sheet such as a polyethylene sheet or a polyethylene sheet laminated nonwoven fabric and a liquid permeable front-surface sheet such as a nonwoven fabric or a liquid permeable plastic sheet, and a side sheet is arranged on both side parts on a skin side along the longitudinal direction, respectively, has been known.

Absorbent articles of this kind have gone through various improvements, and there exists an absorbent article whose side sheet is provided with embosses in order to prevent lateral leakage, improve the flexibility, and improve the feel against the skin (see, for example, the undermentioned Patent Literatures 1 to 3). In the undermentioned Patent Literature 1, an absorbent article is disclosed, wherein an emboss of a complex wave-like line, obtained by superposing a substantially simple harmonic wave of a relatively short period on a substantially simple harmonic wave of a relatively long period, is imparted on the side nonwoven fabrics, respectively, from a front surface side in a manner so as to run along the longitudinal direction of the absorbent article, cross over and back a side terminal edge of the absorbent article, and be linearly symmetrical with the central line of the absorbent article in the longitudinal direction, and the substantially simple harmonic wave component of relatively long period of the emboss is arranged so as to curve convexly towards the inside at least within a region corresponding to a blood discharge part.

Further, in the undermentioned Patent Literature 2, an absorbent article is disclosed, wherein a plurality of emboss patterns of a substantially wave-line shape are formed on a side sheet by arranging curved emboss lines in the longitudinal direction, and an emboss pattern with a shape different from that of the emboss line constituting the emboss pattern is provided between the emboss patterns adjoining in the longitudinal direction.

Furthermore, in the undermentioned Patent Literature 3, an absorbent article is disclosed, wherein an emboss part having a plurality of compressed parts is formed along each side sheet, the emboss part having a first emboss part constituted of a plurality of first compressed parts formed on a front edge side and a back edge side that are the terminal parts of the absorbent article in the longitudinal direction, and a second emboss part constituted of a plurality of second compressed parts formed at a center part in the longitudinal direction, the first emboss part formed to be broader in the width direction than the second emboss part.

PRIOR ART LITERATURES

Patent Literatures

Patent Literature 1: JP 2009-131442 A
Patent Literature 2: JP 2005-323904 A
Patent Literature 3: JP 2008-289622 A

SUMMARY OF THE INVENTION

Technical Problem

However, as for the absorbent article described in Patent Literature 1, since an emboss pattern of a complex wave-line is formed in a continuous line, there was a risk that, when the absorbent article is curved along the curve of a body in the anteroposterior direction while being worn, the absorbent article's flexibility with respect to the body deteriorates due to the stiffness of the emboss.

Furthermore, as for the absorbent article described in Patent Literature 2, while a part obtained by folding back the inside of the side sheet in the width direction to the outside in the width direction is joined by the emboss line and the emboss pattern, the side sheet and a front-surface sheet are joined with an adhesive. Therefore, the side sheet and the front-surface sheet have a structure that causes them to detach easily. Moreover, since the emboss line is formed into a continuous line, there was a risk that the flexibility with respect to a body may deteriorate in the same manner as the absorbent article described in Patent Literature 1.

On the other hand, in the absorbent article described in Patent Literature 3, since the emboss part is intermittently provided, the flexibility with respect to the body is considered to be excellent when the absorbent article is curved along the curve of the body in the anteroposterior direction while being worn. However, since the emboss in the center part is formed to be narrower compared to the front- and back-end parts, the joining strength of the center part is weak, and there was likelihood of the adhesion breaking due to a large movement of a body. If the adhesion between the side sheet and the front-surface sheet breaks, the bodily fluid absorbed by the absorber and diffused in a lateral direction seeps out to the surface from the gap portion where the joint is broken, worsening the feel during wearing or causing leakage.

Therefore, a primary object of the present invention is to provide an absorbent article that joins the side sheet and the front-surface sheet strongly to prevent the detachment thereof, fits flexibly to the body, and has improved feel against the skin.

Solution to Problem

According to a first aspect, an absorbent article is provided, in which a side sheet is arranged on both side parts on a skin side of a liquid permeable front-surface sheet along a longitudinal direction, respectively;

a side emboss is formed on a skin side of a laminated part of the side sheet and the liquid permeable front-surface sheet by fusing the side sheet and the liquid permeable front-surface sheet, the side emboss sinking in toward a non-skin side; and the side emboss comprises a plurality of large embosses formed to have a relatively larger area that are arranged at equal intervals to align linearly along the longitudinal direction of the absorbent article, and between the adjacent large embosses, a plurality of small embosses formed to have a relatively small area that are arranged in a wave-like shape along the longitudinal direction of the absorbent article with intervals, separated from the large embosses.

In the first aspect, since a side emboss sinking in towards a non-skin side and fusing the side sheet and the liquid permeable front-surface sheet is formed on a skin side of a laminated part of the side sheet and the liquid permeable front-surface sheet, the side sheet is strongly fixed to the liquid permeable front-surface sheet, and detachment thereof can be surely prevented even when subjected to a large movement of the body while being worn.

Furthermore, since the side emboss is formed to have a relatively larger area and has a plurality of large embosses arranged at equal intervals to align linearly along the longitudinal direction of the absorbent article, the side sheet and the liquid permeable front surface are strongly adhered by the large emboss even in a portion where the movement of the body is large, thereby preventing detachment thereof.

Furthermore, a plurality of small embosses formed to have relatively small area are arranged between adjoining large embosses and separated from the large emboss, with intervals and in a wave pattern along the longitudinal direction of the absorbent article. Therefore, compared with the case where a continuous linear emboss line is formed, deformation along the curve of the body in the anteroposterior direction of the body occurs more easily while being worn and the fitting to the shape of the body becomes flexible, thereby enhancing flexibility with respect to the body. Moreover, since a plurality of small embosses are arranged in a wave pattern with intervals, the feel against the skin with respect to friction in the anteroposterior direction of the absorbent article can be made softer. Specifically, if the embosses are arranged linearly in the longitudinal direction of the absorbent article, since the small embosses always contact always the same portion with respect to the movement of the body in the anteroposterior direction of the absorbent article, the feel against the skin worsens. However, by arranging the embosses in a wave pattern along the longitudinal direction of the absorbent article, since a part of a skin with which the small embosses contact is dispersed, the feel against the skin can be improved.

According to a second aspect, the absorbent article described in the first aspect is provided, wherein the small embosses are arranged within a width sandwiched by a straight line connecting the exterior ends of the large emboss in a width direction and a straight line connecting the interior ends thereof.

In the second aspect, since the small embosses are arranged within a width sandwiched by a straight line connecting the exterior ends of the large emboss in a width direction and a straight line connecting the interior ends thereof, when a force that may cause detachment is applied on the side sheet, a plurality of the large embosses resist to the detachment, thereby enhancing the joining strength. If the small embosses are arranged outside the width of the large emboss, the small emboss receives the force first, becoming susceptible to detachment.

According to a third aspect, the absorbent article described in any one of the first or second aspects is provided, wherein an interval between the adjacent large embosses is 20 to 50 mm.

In the third aspect, a predetermined range is defined as an interval between the adjacent large embosses. If the interval is smaller than 20 mm, the hardness of the fused part tends to be felt, resulting in worse feel against the skin. Furthermore, if the interval exceeds 50 mm, there is a risk that the joining strength may not be secured.

According to a fourth aspect, the absorbent article described in any one of the first to third aspects is provided, wherein the small embosses are arranged on a virtual line in the shape of a substantially simple harmonic wave having a wavelength of ½ to ⅛ relative to the length in the longitudinal direction of the absorbent article.

In the fourth aspect, since the small embosses are arranged on a virtual line in the shape of a substantially simple harmonic wave having a wavelength of ½ to ⅛ relative to a length in the longitudinal direction of the absorbent article, the small embosses are positioned such that they surely do not contact the same portion of the body with respect to a movement of the body in the anteroposterior direction of the absorbent article, thereby making the feel against the skin softer.

According to a fifth aspect, the absorbent article described in any one of the first to fourth aspects is provided, wherein the width dimension of the large emboss is 50% of an overlapping width of the side sheet and the liquid permeable front-surface sheet or larger.

In the fifth aspect, since the width dimension of the large emboss is set to 50% of the overlapping width of the side sheet and the liquid permeable front-surface sheet or larger, the side sheet and the liquid permeable front-surface sheet are strongly joined by the large emboss, thereby surely preventing the detachment thereof.

According to a sixth aspect, the absorbent article described in any one of the first to fifth aspects is provided, wherein the side sheet and the liquid permeable front-surface sheet are adhered with an adhesive except for a part where the large emboss is applied.

In the sixth aspect, since the side sheet and the liquid permeable front-surface sheet are adhered with an adhesive except for a part where the large emboss is applied, the side sheet and the liquid permeable front-surface sheet can be further strongly fixed due to, in addition to fusing by the emboss, the adhesion effect of the adhesive. Since coating a part where the large emboss is applied to with an adhesive will further increase the hardness, the part where the large emboss is applied to shall not be coated with an adhesive.

According to a seventh aspect, the absorbent article described in any one of the first to sixth aspects is provided, wherein the large emboss is formed such that its area is asymmetrical with respect to the width direction of the absorbent article, and the side with relatively small joining strength is oriented towards the direction in which the wave form formed by the small embosses protrudes in the width direction of the absorbent article, and the side with relatively large joining strength is oriented towards the direction opposite thereto.

In the seventh aspect, the orienting direction of the large emboss in the case where the large emboss is formed in a shape with an area that is asymmetrical with respect to a width direction of the absorbent article is defined. Specifically, the side with relatively small joining strength (having small fusion area) is oriented towards the direction in which the wave form formed by the small embosses protrudes in the width direction of the absorbent article, and the side with relatively large joining strength (having large fusion area) is oriented towards the direction opposite thereto. Therefore, the side where the joining strength of the large emboss is weaker can be compensated with the small embosses, thereby preventing the detachment of the side sheet. Moreover, from the viewpoint of appearance design of the side emboss, it can be visually stressed that the joining strength is substantially equal over the entire length.

Effect of the Invention

As was detailed above, according to the present invention, a side sheet and a front-surface sheet can be strongly joined together to prevent detachment, and can fit flexibly to a body and have soft feel against the skin.

BRIEF DESCRIPTION OF DRAWINGS

FIG. 1 is a partially-broken developed view of a sanitary napkin 1 according to the present invention.

FIG. 2 is an arrow view taken along a II-II line of FIG. 1.

FIG. 3(A) to (C) are enlarged plan views of a side emboss 10 according to a modification.

FIGS. 4(A), (B) are enlarged plan views of an overlapping part of the side sheet 7 and the liquid permeable front-surface sheet 3 according to a modification.

FIG. 5 is a developed view of the sanitary napkin 1 according to the modification.

FIG. 6 is a developed view of the sanitary napkin 1 according to the modification.

DESCRIPTION OF EMBODIMENTS

In what follows, an embodiment of the present invention will be detailed with reference to the drawings.

(Basic Structure of Sanitary Napkin 1)

A sanitary napkin 1 according to the present invention is, as shown in FIG. 1 and FIG. 2, constituted of a liquid impermeable back-surface sheet 2 made of a polyethylene sheet, a polypropylene sheet or the like, a liquid permeable front-surface sheet 3 that rapidly permeates mensural blood or vaginal discharge, an absorber 4 made of cotton pulp or synthetic pulp interposed between both sheets 2, 3, a wrapping sheet 5 made of a crepe sheet or a nonwoven fabric surrounding the absorber 4 to retain the shape of the absorber 4 and improve the diffusion property thereof, and side sheets 7, 7 arranged on both sides on a skin contact side along the longitudinal directions, respectively. Furthermore, in the surroundings of the absorber 4, an outer periphery flap part, in which the absorber 4 does not exist on its outer periphery, is formed by joining the outer edge parts of the liquid impermeable back-surface sheet 2 and the liquid permeable front-surface sheet 3 by an adhesive such as a hot-melt or an adhesion means such as a heat seal or ultrasonic seal in the front- and back-end edge parts of the absorber 4 in the napkin's longitudinal direction, and also joining the liquid impermeable back-surface sheet 2 and the side sheet 7 which laterally extend past the side edge of the absorber 4 by an adhesive such as a hot-melt or adhesion means such as a heat seal or ultrasonic seal on both such edge parts.

To describe a structure of the sanitary napkin 1 in more detail:

a sheet material having at least water sealing property such as an olefin-based resin sheet such as polyethylene or polypropylene is used as the liquid impermeable back-surface sheet 2. Apart from these, however, a laminated nonwoven fabric obtained by laminating a nonwoven fabric on a polyethylene sheet or the like, or alternatively, a nonwoven fabric sheet whose liquid impermeability is substantially secured by interposing a water-proof film (in this case, the liquid impermeable back-surface sheet is formed from the water-proof film and the nonwoven fabric form) may be used. In recent years, from the viewpoint of the stuffiness prevention, liquid permeable ones tend to be used. The water-proof and moisture permeable sheet material is a microporous sheet obtained by molding a sheet by melt extruding an inorganic filler in an olefin-based resin such as polyethylene or polypropylene and, thereafter, stretching it in a monoaxial or biaxial direction.

Then, as the liquid permeable front-surface sheet 3, a nonwoven fabric is suitably used. As a raw material fiber constituting the nonwoven fabric, for example, synthetic fibers whose examples include olefin-based fibers such as polyethylene or polypropylene fibers, polyester-based fibers or polyamide-based fibers, or alternatively, recycled fibers such as rayon or cupra, or natural fibers such as cotton may be used, and nonwoven fabrics obtained with an appropriate processing method such as a spunlace method, a spunbond method, a thermal bonding method, a melt-blown method, or a needle punching method may be used. Among these processing methods, the spunlace method excels in flexibility, the spun bond method excels for having rich draping property, and the thermal bond method and the air-through method excel in providing bulkiness and high compression restorability. Alternatively, conjugated fibers, such as that of a core-sheath type fiber having a high-melting-point fiber as a core and a low-melting-point fiber as a sheath, a side-by-side type fiber, or a split type fiber, may be used. Preferably, a synthetic fiber is preferably blended into the liquid permeable front-surface sheet 3 in order to achieve fusion with the side sheet 7.

As the absorber 4 interposed between the liquid impermeable back-surface sheet 2 and the liquid permeable front-surface sheet 3, one in which a superabsorbent resin is mixed into the pulp, or alternatively, one in which a chemical fiber as well as a superabsorbent resin is mixed into the pulp can be used, for example. As shown in the drawing, the absorber 4 is desirably surrounded by the wrapping sheet 5 to retain the shape, disperse the menstrual blood rapidly, and prevent reflux of the absorbed menstrual blood. As the pulp, chemical pulp obtained from timber, cellulose fibers such as dissolving pulp, and artificial cellulose fibers such as rayon or acetate may be used. Softwood pulp having a fiber length longer than that of hardwood pulp is suitably used in view of function and price. Furthermore, as the absorber 4, an air-laid absorber that can reduce a volume or a polymer sheet obtained by arranging a superabsorbent resin between two layers of nonwoven fabric may be used.

Further, a synthetic fiber may be mixed in the absorber 4. As the synthetic fiber, for example, olefin-based synthetic fibers such as polyethylene or polypropylene, polyester-based synthetic fibers such as polyethylene terephthalate or polybutylene terephthalate, polyamide-based synthetic fibers such as nylon, and copolymers of these may be used, while those obtained by mixing two kinds among the above may be used. Furthermore, a conjugated fiber, such as a core-sheath type fiber having a high-melting-point fiber as a core and a low-melting-point fiber as a sheath, a side-by-side type fiber, or a split-type fiber, may also be used. If the synthetic fiber is a hydrophobic fiber, it is desirable to use it after surface-treating with a hydrophilizing agent in order to impart affinity to bodily fluid.

Examples of superabsorbent resins include substances obtained by partially crosslinking water-swellable polymers such as crosslinked products of polyacrylic acid salt, a self-crosslinked polyacrylic acid salt, a saponified product of acrylic acid ester-vinyl acetate copolymer crosslinked product, an isobutylene-maleic anhydride copolymer crosslinked product, a polysulfonate crosslinked product, polyethylene oxide, and polyacryl amide. Among these, acrylic acid- or acrylic acid salt-based products having an excellent water absorption amount and water absorption rate are suitable. A water absorption power and water absorption rate of the superabsorbent resin having the above-described water absorption property can be adjusted by controlling the crosslinking density and the crosslinking density gradient during the manufacturing process. The content of the superabsorbent resin is desirably set to 5 to 60% of the absorber weight. If the content of the superabsorbent resin is less than 5%, sufficient absorptivity cannot be imparted, and if the content exceeds 60%, there would be no entanglement between pulp fibers and lead to a decline in the sheet strength, thereby resulting in breaks or cracks caused easily.

In the case where the wrapping sheet 5 surrounding the absorber 4 is provided like in the present example, resultantly the wrapping sheet 5 is interposed between the liquid permeable front-surface sheet 3 and the absorber 4. In the case where the wrapping sheet 5 is formed of crepe paper, the wrapping sheet 5 having excellent absorptivity rapidly diffuses the bodily fluid and, at the same, prevents the reflux of the mensural blood or the like.

On the other hand, on both side parts on the skin contact surface side of the present sanitary napkin 1, side sheets 7, 7 are provided along the longitudinal direction of and substantially over the entire length of the napkin 1, respectively. Parts of the side sheets 7, 7 are extended in a lateral direction, and wing-like flaps W, W protruding outside on both side parts of the main body part are formed by a part of the liquid impermeable back-surface sheet 2 extended in the lateral direction in the same manner. The wing-like flaps w, w are used by folding them back towards the outside at a folding line RL (FIF. 1) on the base end part so as to wrap up the crotch of an underwear upon wearing, and are meant for preventing displacement of the napkin 1 from the underwear by adhering a displacement prevention adhesive layer (not shown in the drawing) provided on an outer surface of the liquid impermeable back-surface sheet 2 of the wing-like flap W to the outer surface of the underwear.

As the side sheet 7, a water-repellent treated nonwoven fabric or a hydrophilic treated nonwoven fabric may be used in view of the function deemed important. For example, when preventing permeation of the mensural blood or vaginal discharge or enhancing the feel against the skin is deemed important, a water-proof treated nonwoven fabric coated with a silicone-based, paraffin-based, or alkylchromic chloride-based water repellent is desirable. Alternatively, if the absorptivity of the mensural blood or the like in the wing-like flaps W, W is deemed important, it is desirable to use a hydrophilic-treated nonwoven fabric imparted with hydrophilic property by making the synthetic fiber swellable or porous and utilizing the capillary phenomenon via methods such as polymerizing by making a compound having a hydroxyl group such as an oxidation product of polyethylene glycol coexist in the production process of the synthetic fiber, or treating with a metal salt such as stannic chloride, thereby partially dissolving the surface and making it porous to precipitate a metal hydroxide. Preferably, synthetic fiber is blended in the side sheet 7 to achieve fusion with the liquid permeable surface sheet 3.

The inner side in the width direction of the side sheet 7 is laminated on the skin side on the outer side in the width direction of the liquid permeable front-surface sheet 3, and such side sheet 7 and liquid permeable front-surface sheet 3 are joined in these laminated parts. As shown in FIG. 1, from the viewpoint of securing the joining strength thereof and preventing the lateral leakage of the bodily fluid, an overlapping width M of the side sheet 7 and the liquid permeable front-surface sheet 3 is set preferably to 5 to 15 mm.

(Side Emboss)

On the skin side of the laminated part of the side sheet 7 and the liquid permeable front-surface sheet 3, a side emboss 10 that sinks in toward a non-skin side and is obtained by fusing the side sheet 7 and the liquid permeable front-surface sheet 3 is formed. That is, the side sheet 7 and the liquid permeable front-surface sheet 3 are joined by fusing a part of the fiber of the side sheet 7 and the liquid permeable front-surface sheet 3 during the processing of the side emboss 10 wherein compression is applied from a skin contact surface side of the side sheet 7. The side emboss 10 formed on each of right and left side sheets 7 is preferably arranged symmetrically with respect to a central line CL in the longitudinal direction of the sanitary napkin 1.

In order to form the side emboss 10, after arranging the side sheet 7 on both sides on a skin side of the liquid permeable front-surface sheet 3, respectively, the side sheet 7 and the liquid permeable front-surface sheet 3 are integrally compressed from the outer surface side of the side sheet 7 by passing the sheets between an emboss roll provided with an emboss convex part on the surface and an anvil roll having a flat surface. The liquid permeable front-surface sheet 3 and side sheet 7 may be joined only by the side emboss 10, or alternatively, may be joined, by an adhesive coated on a predetermined region described later in addition to the emboss.

Upon fusing of the side sheet 7 and the liquid permeable front-surface sheet 3, heat sealing in which heat is applied during the emboss compression is preferably used, but ultrasonic fusion which ultrasonic waves are irradiated during the emboss compression may also be used.

As shown in FIG. 1, the side emboss 10 is formed such that a plurality of large embosses 11, 11 . . . formed to have a relatively larger area are arranged at equal intervals to align linearly along the napkin's longitudinal direction, while a plurality of small embosses 12, 12 . . . formed to have a relatively small area are arranged between the adjacent large embosses 11, 11 in a wave shape along the napkin's longitudinal direction with intervals, distanced from the large embosses 11. That is, the side emboss 10 forms a pattern such that a plurality of small embosses 12, 12 . . . are arranged in a wave shape between a plurality of the large embosses 11, 11 . . . arranged linearly along the longitudinal direction of the sanitary napkin 1 with equal intervals.

When the large embosses 11, 11 . . . are arranged to align linearly along the napkin's longitudinal direction, this means that when a line $L_o$, which connects the outside ends in the width direction (width direction of the sanitary napkin 1) of all large embosses 11, 11 . . . arranged on one side with respect to center line CL in the longitudinal direction as the boundary, and a line $L_i$, which connects the inside ends thereof, are drawn, these $L_o$, $L_i$ are formed of a straight line in parallel with the center line CL in the napkin's longitudinal direction, as shown in FIG. 1. Furthermore, when the large embosses 11, 11 . . . are arranged at equal intervals, this means that the intervals S between adjacent large embosses 11, 11 (intervals between end parts of the large embosses 11, 11 in the napkin's longitudinal direction) are substantially the same.

When the plurality of small embosses 12, 12 . . . are arranged in a wave shape along the longitudinal direction of the sanitary napkin 1, this means that a virtual line V passing through the small embosses 12 is arranged so as to snake through the napkin's width direction, and this is a concept including not only cases where the virtual line V constitutes of smooth curves such as a simple harmonic wave, but also cases where the line V constitutes of a folded line such as a zigzag line.

In the present sanitary napkin 1, since the side emboss that sinks in toward a non-skin side is formed on a skin side of a laminated part of the side sheet 7 and the liquid permeable front-surface sheet 3, the side sheet 7 is strongly fixed to the liquid permeable front-surface sheet 3. Therefore, even when subjected to a large movement of the body while being worn, the detachment thereof can surely be prevented. That is, since many of the side sheet and front-surface sheet in the conventional absorbent articles are adhered together only by an adhesive, the joining by the side embosses 10 obtained by fusing the nonwoven fabrics can fix the sheets stronger compared with the joining by the adhesive only, thereby preventing the detachment of the sheets.

Furthermore, since the side emboss 10 has a plurality of large area embosses 11, 11 . . . that are formed to have a relatively larger area and arranged at equal intervals to align linearly along the napkin's longitudinal direction, such large embosses 11 . . . strongly joins the side sheet 7 to the liquid permeable front-surface sheet 3 even in parts that are subjected to a large movement of the body, such as the inseam part which is readily influenced by the movement of legs, and the side sheet 7 can be prevented from detaching from the liquid permeable front-surface sheet 3.

Furthermore, since a plurality of small embosses 12, 12 . . . that are formed to have a relatively small area are arranged between adjacent large embosses 11, 11 in a wave shape along the napkin's longitudinal direction with intervals, distanced from the large emboss, by providing non-emboss parts between the small embosses 12, 12 as well as between the small emboss 12 and the large emboss 11, respectively, compared with the case where a continuous linear emboss line is formed, deformation along the curve of the body in the anteroposterior direction while being worn easily occurs, and the sanitary napkin 1 fits flexibly to a shape of the body, thereby enhancing the flexibility with respect to the body.

Furthermore, since a plurality of small embosses 12, 12 . . . are arranged in a wave shape with intervals, the feel against the skin with respect to the friction in the anteroposterior direction of the sanitary napkin 1 can be softened. Specifically, if the small embosses 12 are arranged linearly in the longitudinal direction of the sanitary napkin 1, when a relative movement of the body to the anteroposterior direction of the sanitary napkin 1 is generated, since the small embosses always contact the same part or the body, the hardness of the emboss tends to be felt, resulting in worse feel against the skin. By contrast, in the present sanitary napkin 1, since the small embosses 12, 12 . . . are arranged in a wave shape in the napkin's longitudinal direction, each of the small embosses 12 contacts a different part of the body, thereby dispersing the part that contacts the skin, making the feel against the skin softer.

In what follows, the side emboss 10 will be described in more detail. The large emboss 11 may be, as shown in FIG. 1, formed in such a manner that a plurality of concave parts are arranged in vicinity to each other and these concaves forms one pattern as a group, or in such a manner that an integral concave forms one pattern (see FIG. 3). The shape of the large emboss 11 may be formed to be any shape, such as a flower shape shown in FIG. 1, or a triangle shape, a heart shape, a crescent shape or the like shown in FIG. 3.

On the other hand, the small emboss 12 is preferably formed to be a relatively simple shape, since it is formed to have a small area. For example, as shown in FIG. 1 and FIG. 3, it may be a round shape, a diamond shape, or a star shape.

The ratio (area ratio) between the area of the large emboss 11 and the area of the small emboss is set to "the area of the large emboss 11":"the area of the small emboss 12"=4:1 to 50:1, and preferably to 5:1 to 20:1. By setting the area ratio in this range, the joining strength of the large emboss 11 and the small emboss 12 can be sufficiently secured, and the worsening of the feel against the skin when the small emboss 12 contacts with the skin surface can be prevented.

As shown in FIG. 1, an interval S between the adjacent large embosses 11, 11 in the napkin's longitudinal direction is preferably set to 20 to 50 mm. When the interval S is smaller than 20 mm, the hardness of the fused part tends to be felt, resulting in worse feel against the skin. On the other hand, when the interval S exceeds 50 mm, there is a risk that joining strength may not be secured.

The width dimension of the large emboss 11 (the dimension of the large emboss 11 in a napkin's width direction) is set to 50% of an overlapping width M of the side sheet 7 and the liquid permeable front-surface sheet 3 or larger, and preferably to 50 to 90% thereof, as shown in FIG. 1. This causes the side sheet 7 and the liquid permeable front-surface sheet 3 to join strongly by the large emboss 11, and the detachment thereof can be surely prevented. The large emboss 11 is preferably formed within the range of the overlapping width M, and forming it in a manner so as to stick outward from the overlapping width M in the width direction is not preferable.

The large emboss 11 is preferably arranged at a center part in the napkin's width direction relative to the overlapping width M of the side sheet 7 and the liquid permeable front-surface sheet 3, but may be arranged at a position biased a little on an inner side than the above.

The large emboss 11 is preferably formed in a shape where the dimensions thereof in the napkin's width direction and the longitudinal direction are substantially the same, and this aspect ratio is preferably set to about 0.8 to 1.2. This can secure the joining strength, and the napkin curves easily in the napkin's longitudinal direction while hardly being subjected to the stiffness of the large emboss 11.

In the case where the large emboss 11 is formed in a shape having directionality, although the direction with which large emboss 11 is arranged is freely selected, as will be further detailed later, it is preferable to arrange the large embosses alternately such that the adjacent large embosses 11, 11 are in a reverse direction in the napkin's width direction. This makes the joining strength to the napkin's width direction substantially equal, and, also from the viewpoint of appearance design, it can be visually stressed that the joining part is uniformly joined without biases.

As shown in FIG. 1 and FIG. 3, as for the alignment direction when the area of the large emboss 11 is formed in a shape asymmetrical with respect to the width direction of the sanitary napkin 1, it is preferable that the side with relatively small joining strength is aligned in a direction in which the wave shape formed by the small embosses 12, 12 . . . projects in the width direction of the sanitary napkin 1, and the side with relatively large joining strength is aligned in the direction on the opposite side thereto. The large emboss 11 shown in FIG. 1 is formed of a flower shape where 5 elliptical flower petals are arranged radially, and the side with two flower petals is formed to have larger joining strength (fused area) than the side with one flower petal. In the same manner, also for (A) the triangle shape, (B) the heart shape, and (C) the crescent shape shown in FIG. 3, one side is formed to have a larger joining strength (fused area) than the other side. By arranging the large emboss 11 in such direction, since a convex part of the small embosses 12, 12 . . . arranged in a wave shape is located on a side where the joining strength of the large emboss 11 is low, unbalance of the joining strength of the large emboss 11 can be compensated by the small embosses, thereby preventing detachment of the side sheet 7, and in terms of the appearance design of the side emboss 10, it can be visually stressed that the joining strength is substantially uniform over the entire length.

The small embosses 12 are preferably arranged within the width of the large emboss 11. That is, the small embosses 12 are formed, as shown in FIG. 1, within the width sandwiched by a straight line $L_o$ connecting the outside ends of the large emboss 11 in the width direction and a straight line Li connecting the inside ends thereof. Accordingly, with regards to the side emboss 10, all of the large embosses 11 and small embosses 12 are arranged within a belt-like width with the straight lines $L_o$ and $L_i$ as side ends thereof. Thus, when a force that causes the detachment of the side sheet 7 is applied, a plurality of large embosses 11, 11 . . . resist to the detachment, thereby enhancing the joining strength of the side sheet 7 and the liquid permeable front-surface sheet 3. By contrast, when the small emboss 12 is arranged more outside than the width dimension of the large emboss 11, the small emboss 12 receives the force that causes the detachment of the side sheet 7 first, and the side sheet 7 is easily detached.

Preferably, about 2 to 15 small embosses 12 are arranged between adjacent large embosses 11, 11. The number of the small embosses 12 arranged depends largely on a separation distance between the adjacent large embosses 11, 11, and, the small embosses are arranged within a range capable of securing sufficient joining strength, while enhancing the flexibility by securing to a certain extent the separation distance between the small embosses 12, 12.

An interval in the napkin's longitudinal direction of the adjacent small embosses 12, 12 (an interval between non-emboss parts) is preferably set to about 2 to 10 mm. When the interval is set to be smaller than 2 mm, the small embosses 12 are too close to each other such that they generate an effect similar to that when a straight line is formed. On the other hand, when the interval exceeds 10 mm, it becomes impossible to secure the joining strength.

The small embosses 12, 12 . . . are preferably arranged on a virtual line V in the shape of a substantially simple harmonic wave having a wavelength $\lambda$ of ½ to ⅛, preferably ⅓ to ⅐, relative to the length of the sanitary napkin 1 in the longitudinal di section. This surely prevents the small embosses 12 from contacting the same site of the body with respect to a movement of the body in the anteroposterior direction of the sanitary napkin 1, and a part of the skin to which the small emboss 12 contact can be surely dispersed, thereby making the feel against the skin softer. As shown in FIG. 1, the large emboss 11 may be located at an apex of a convex part towards the width direction with respect to the virtual line V of the substantially simple harmonic wave formed by the small embosses 12, or may be located at an intermediate part as will be described later (see FIG. 5).

The side sheet 7 and the liquid permeable front-surface sheet 3 may be joined by only the side emboss 10, or alternatively, a predetermined part may be adhered with an adhesive to further enhance the joining strength between these sheets and to reduce the gap in the joining part in a non-emboss part, as shown in FIG. 4. The adhesion part 13 is, as shown in FIG. 4(A), preferably formed in a part except for a part where the large emboss is applied. When the adhesion part 13 is provided so as to overlap the part where the large emboss is applied, since the hardness due to curing of the adhesive adds to the hardness due to the fusion of the sheets, the hardness of the large emboss 11 is further increased, and an unpleasant feeling tends to be caused during wearing. Alternatively, the adhesion part 13 may be formed a part except for a part where the large emboss 11 and small emboss 12 are applied, as shown in the same FIG. 4(B). In this case, the adhesion part 13 is preferably arranged such that, between adjacent large embosses 11, at least either the small emboss 12 or the adhesion part 13 is always applied with respect to the width direction of the sanitary napkin 1. This diminishes the gap at the joining part in the napkin's width direction, and the leaking of the bodily fluid can be prevented.

As a modified example of the wave-like pattern of the small embosses 12, as shown in FIG. 5, a pattern may be arranged such that, between adjacent large embosses 11, 11, the small embosses 12, 12 . . . are arranged on a virtual line having a substantially simple harmonic wave of substantially one period having the center part of the large embosses 11, 11 on both sides as its base point and such small embosses are repeatedly moved parallel in the napkin's longitudinal direction.

Furthermore, in the above embodiment, a so-called daytime sanitary napkin 1 wherein the lengths of the main body part extending farther than the wing-like flap W towards the front side and back side are substantially the same, respectively, was described. However, as shown in FIG. 6, the same may be applied to a so-called nighttime sanitary napkin wherein the back side is formed to be longer than the front side.

REFERENCE SIGNS LIST

1 . . . SANITARY NAPKIN,
2 . . . LIQUID IMPERMEABLE BACK-SURFACE SHEET,
3 . . . LIQUID PERMEABLE FRONT-SURFACE SHEET,
4 . . . ABSORBER,
5 . . . WRAPPING SHEET,
7 . . . SIDE SHEET,
10 . . . SIDE EMBOSS,
11 . . . LARGE EMBOSS,
12 . . . SMALL EMBOSS,
13 . . . ADHESION PART

The invention claimed is:
1. An absorbent article comprising:
a liquid permeable front-surface side sheet,
a side sheet arranged on both side parts of the liquid permeable front-surface sheet on a skin side along a longitudinal direction, respectively, and
a side emboss formed on a skin side of a laminated part of the side sheet and the liquid permeable front-surface sheet by fusing the side sheet and the liquid permeable front-surface sheet, the side emboss sinking in toward a non-skin side,
wherein the side emboss comprises a plurality of large embosses formed to have a relatively larger area that are arranged at equal intervals to align linearly along the longitudinal direction of the absorbent article, and between the adjacent large embosses, a plurality of small embosses formed to have a relatively small area that are arranged on a virtual line in the shape of a substantially simple harmonic wave along the longitudinal direction of the absorbent article with intervals, wherein the small embosses are spaced from the large embosses,
wherein the large embosses are formed such that an area of the large embosses is asymmetrical with respect to the width direction of the absorbent article, such that the large embosses have a side with a relatively small joining strength and an opposing side with a relatively large joining strength, and the large embosses are arranged alternatively such that adjacent large embosses are oriented in reverse directions in the width direction of the absorbent article, wherein the side of the large embosses with relatively small joining strength is aligned in a direction in which the virtual line formed by the small embosses protrudes in the width direction of the absorbent article, the large embosses oriented such that the side with relatively small joining strength is located at every apex of the virtual line in the shape of the substantially simple harmonic wave formed by the small embosses.

2. The absorbent article according to claim 1, wherein the small embosses are arranged within a width sandwiched by a first straight line and a second straight line,
wherein the first straight line connects an interior end of a first one of the large embosses and an interior end of a second one of the large embosses, and
wherein the second straight line connects an exterior end of the first one of the large embosses and an exterior end of the second one of the large embosses.

3. The absorbent article according to claim 1, wherein an interval between the adjacent large embosses is 20 to 50 mm.

4. The absorbent article according to claim 1, wherein the virtual line has a wavelength of ½ to ⅛ relative to a length of the absorbent article in the longitudinal direction.

5. The absorbent article according to claim 1, wherein a width dimension of the large embosses is 50% of an overlapping width of the side sheet and the liquid permeable front-surface sheet or larger.

6. The absorbent article according to claim 1, wherein the side sheet and the liquid permeable front-surface sheet are adhered with an adhesive except for a part to which the large embosses are applied.

* * * * *